United States Patent
Maiorano

(10) Patent No.: US 11,203,757 B2
(45) Date of Patent: Dec. 21, 2021

(54) USE OF RAD18 INHIBITORS IN THE TREATMENT OF TUMORS

(71) Applicant: Centre National De La Recherche Scientifique, Paris (FR)

(72) Inventor: Domenico Maiorano, Saint Martin de Londres (FR)

(73) Assignee: Centre National de la Recherche Scientifique, Paris (FR)

(*) Notice: Subject to any disclaimer, the term of this patent is extended or adjusted under 35 U.S.C. 154(b) by 39 days.

(21) Appl. No.: 16/297,181

(22) Filed: Mar. 8, 2019

(65) Prior Publication Data

US 2019/0194664 A1 Jun. 27, 2019

Related U.S. Application Data

(63) Continuation of application No. 15/536,437, filed as application No. PCT/EP2015/080883 on Dec. 21, 2015, now abandoned.

(30) Foreign Application Priority Data

Dec. 23, 2014 (EP) ..................... 14307151

(51) Int. Cl.
| | |
|---|---|
| C12N 15/113 | (2010.01) |
| C12Q 1/6886 | (2018.01) |
| C07K 16/18 | (2006.01) |
| A61K 31/255 | (2006.01) |
| A61K 31/4745 | (2006.01) |
| A61K 31/555 | (2006.01) |
| A61K 31/7105 | (2006.01) |
| A61K 31/713 | (2006.01) |
| C12N 9/00 | (2006.01) |
| C07K 16/40 | (2006.01) |
| A61K 33/243 | (2019.01) |
| A61K 31/381 | (2006.01) |
| G01N 33/574 | (2006.01) |

(52) U.S. Cl.
CPC ........ *C12N 15/1137* (2013.01); *A61K 31/255* (2013.01); *A61K 31/381* (2013.01); *A61K 31/4745* (2013.01); *A61K 31/555* (2013.01); *A61K 31/713* (2013.01); *A61K 31/7105* (2013.01); *A61K 33/243* (2019.01); *C07K 16/18* (2013.01); *C07K 16/40* (2013.01); *C12N 9/93* (2013.01); *C12N 15/113* (2013.01); *C12Q 1/6886* (2013.01); *C12Y 203/02* (2013.01); *C12Y 603/02* (2013.01); *G01N 33/57496* (2013.01); *C12N 2310/14* (2013.01); *C12N 2320/31* (2013.01); *C12Q 2600/106* (2013.01); *C12Q 2600/158* (2013.01); *G01N 2333/9108* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 2009/0028861 A1* | 1/2009 | Takagi | ................. | G01N 33/574 424/138.1 |
| 2013/0177546 A1 | 7/2013 | Hoelz | | |

FOREIGN PATENT DOCUMENTS

WO WO-2009/126970 A1 10/2009

OTHER PUBLICATIONS

Biasoli et al "Glioblastoma Cells Inhibit Astrocytic p53-Expression Favoring Cancer Malignancy" Oncogenesis vol. 3, pp. 1-6, 2014.
Fan et al "USP7 Inhibitor P22077 Inhibits Neuroblastoma Growth via Inducing p53-Mediated Apoptosis" Cell Death and Disease vol. 4, pp. 1-10, 2013.
Huehis et al "Identification of DNA Repair Pathways that Affect the Survival of Ovarian Cancer Cells Treated with a Poly(ADP-Ribose) Polymerase Inhibitor in a Novel Drug Combination" Molecular Pharmacology, vol. 82, pp. 767-776, 2012.
Liu et al "Tumor Suppressor miR-145 Reverses Drug Resistance by Directly Targeting DNA Damage-Related Gene RAD18 in Colorectal Cancer" Tumor Biology vol. 36, pp. 5011-5019, 2015.
Saberi et al "RAD18 and Poly(ADP-Ribose) Polymerase Independently Suppress the Access of Nonhomologous End Joining to Double-Strand Breaks and Facilitate Homologous Recombination-Mediated Repair" Molecular and Cellular Biology vol. 27, pp. 2562-2571, 2007.
Sasatani et al "RAD18 Activates the G2/M Checkpoint Through DNA Damage Signaling to Maintain Genome Integrity After Ionizing Radiant Exposure" PLOS ONE 2015.
Wagner et al "Cisplatin-Induced DNA Damage Activates Replication Checkpoint Signaling Components that Differentially Affect Tumor cell Survival" Molecular Pharmacology vol. 76, pp. 208-214, 2009.
Xie et al "RAD18 Mediates Resistance to Ionizing Radiation in Human Glioma Cells" Biochemical and Biophysical Research Communications vol. 445, pp. 263-268, 2014.

\* cited by examiner

*Primary Examiner* — Sean McGarry
(74) *Attorney, Agent, or Firm* — Cesari & McKenna, LLP

(57) ABSTRACT

The present invention relates to the use of an inhibitor of Rad18 expression or activity, in treating a tumor or in sensitizing a patient affected with a tumor, to a treatment with an antineoplastic agent that is a DNA damaging chemotherapeutic agent so to both reduce the self renewal of cancer stem cells and increase the DNA damage response thus boosting apoptotic cell death.

Figure 1:
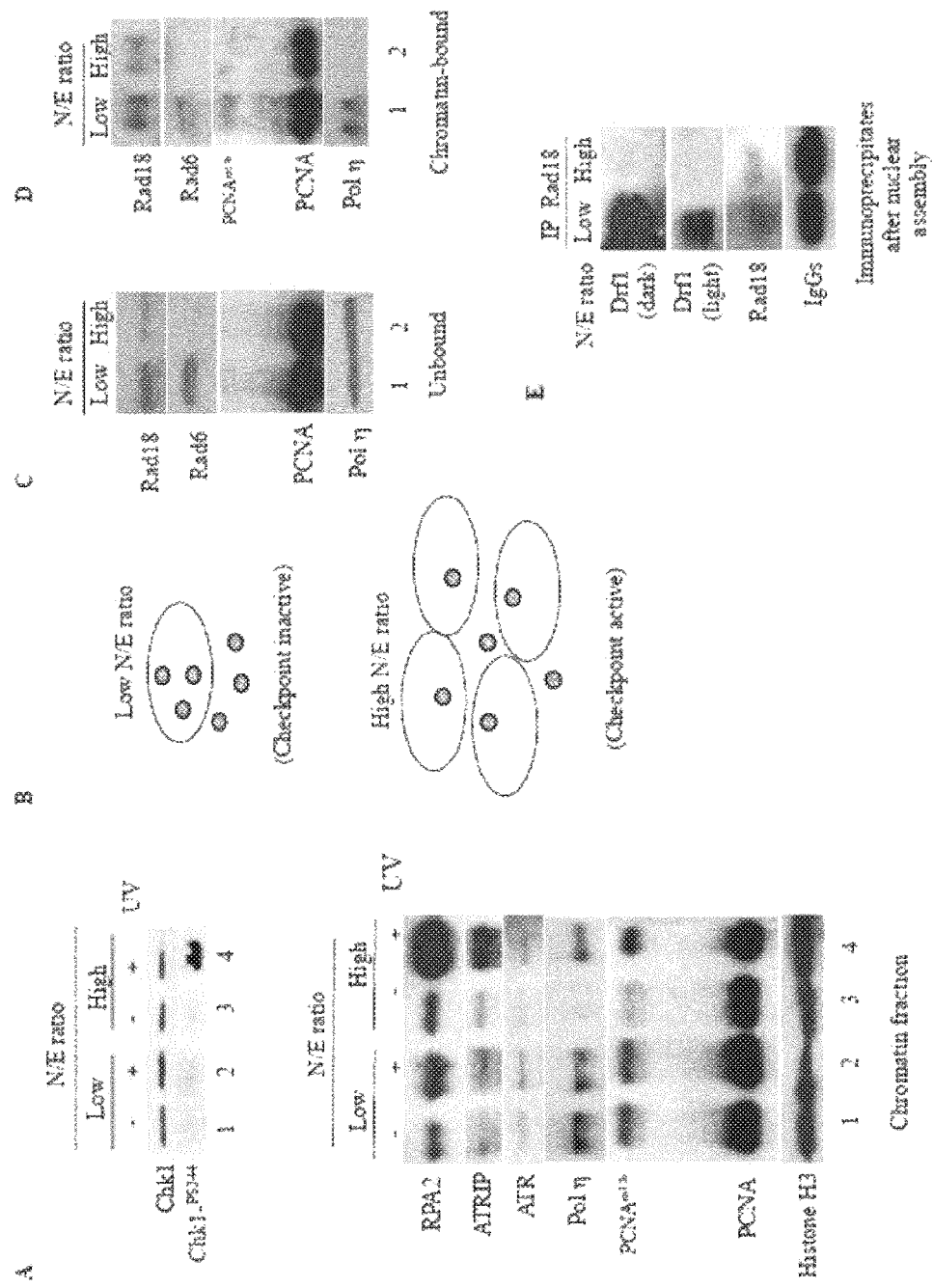

14 Claims, 7 Drawing Sheets
Specification includes a Sequence Listing.

SEQUENCE LISTING

```
<160> NUMBER OF SEQ ID NOS: 3

<210> SEQ ID NO 1
<211> LENGTH: 1669
<212> TYPE: DNA
<213> ORGANISM: Homo sapiens
<220> FEATURE:
<221> NAME/KEY: CDS
<222> LOCATION: (37)..(1524)

<400> SEQUENCE: 1
gtgggtggct gaccccccagc atcctcggga gcgacc atg gac tcc ctg gcc gag     54
                                        Met Asp Ser Leu Ala Glu
                                          1               5 tct cgg tgg cct ccg ggc ctg gca gtc atg aag aca ata gat gat ttg    102
Ser Arg Trp Pro Pro Gly Leu Ala Val Met Lys Thr Ile Asp Asp Leu
             10                  15                  20 ctg cgg tgt gga att tgc ttc gag tat ttc aac att gca atg ata ata    150
Leu Arg Cys Gly Ile Cys Phe Glu Tyr Phe Asn Ile Ala Met Ile Ile
         25                  30                  35 cct cag tgt tca cat aac tac tgc tct ctc tgt ata aga aaa ttt ctg    198
Pro Gln Cys Ser His Asn Tyr Cys Ser Leu Cys Ile Arg Lys Phe Leu
     40                  45                  50 tcc tat aaa act cag tgt cca act tgc tgt gtg act gtc aca gag ccg    246
Ser Tyr Lys Thr Gln Cys Pro Thr Cys Cys Val Thr Val Thr Glu Pro
 55                  60                  65                  70 gat ctg aaa aat aac cgc ata tta gat gaa ctg gta aaa agc ttg aat    294
Asp Leu Lys Asn Asn Arg Ile Leu Asp Glu Leu Val Lys Ser Leu Asn
                 75                  80                  85 ttt gca cgg aat cat ctg ctg cag ttt gct tta gag tca cca gcc aaa    342
Phe Ala Arg Asn His Leu Leu Gln Phe Ala Leu Glu Ser Pro Ala Lys
             90                  95                 100 tct cct gct tct tcc tct tca aag aat ctt gct gtc aaa gta tat act    390
Ser Pro Ala Ser Ser Ser Ser Lys Asn Leu Ala Val Lys Val Tyr Thr
        105                 110                 115 cct gta gcc tcc aga cag tct tta aag cag ggg agc agg tta atg gat    438
Pro Val Ala Ser Arg Gln Ser Leu Lys Gln Gly Ser Arg Leu Met Asp
    120                 125                 130 aat ttc ttg atc aga gaa atg agt ggt tct aca tca gag ttg ttg ata    486
Asn Phe Leu Ile Arg Glu Met Ser Gly Ser Thr Ser Glu Leu Leu Ile
135                 140                 145                 150 aaa gaa aat aaa agc aaa ttc agc cct caa aaa gag gcg agc cct gct    534
Lys Glu Asn Lys Ser Lys Phe Ser Pro Gln Lys Glu Ala Ser Pro Ala
                155                 160                 165 gca aag acc aaa gag aca cgt tct gta gaa gag atc gct cca gat ccc    582
Ala Lys Thr Lys Glu Thr Arg Ser Val Glu Glu Ile Ala Pro Asp Pro
            170                 175                 180 tca gag gct aag cgt cct gag cca ccc tcg aca tcc act ttg aaa caa    630
Ser Glu Ala Lys Arg Pro Glu Pro Pro Ser Thr Ser Thr Leu Lys Gln
```

```
                185                 190                 195
gtt act aaa gtg gat tgt cct gtt tgc ggg gtt aac att cca gaa agt        678
Val Thr Lys Val Asp Cys Pro Val Cys Gly Val Asn Ile Pro Glu Ser
    200                 205                 210 cac att aat aag cat tta gac agc tgt tta tca cgc gaa gag aag aag        726
His Ile Asn Lys His Leu Asp Ser Cys Leu Ser Arg Glu Glu Lys Lys
215                 220                 225                 230 gaa agc ctc aga agt tct gtt cac aaa agg aag ccg ctg ccc aaa act        774
Glu Ser Leu Arg Ser Ser Val His Lys Arg Lys Pro Leu Pro Lys Thr
                235                 240                 245 gta tat aat ttg ctc tct gat cgt gat tta aag aaa aag cta aaa gag        822
Val Tyr Asn Leu Leu Ser Asp Arg Asp Leu Lys Lys Lys Leu Lys Glu
            250                 255                 260 cat gga tta tct att caa gga aat aaa caa cag ctc att aaa agg cac        870
His Gly Leu Ser Ile Gln Gly Asn Lys Gln Gln Leu Ile Lys Arg His
        265                 270                 275 caa gaa ttt gta cac atg tac aat gcc caa tgc gat gct ttg cat cct        918
Gln Glu Phe Val His Met Tyr Asn Ala Gln Cys Asp Ala Leu His Pro
    280                 285                 290 aaa tca gct gct gaa ata gtt caa gaa atc gaa aat ata gag aag act        966
Lys Ser Ala Ala Glu Ile Val Gln Glu Ile Glu Asn Ile Glu Lys Thr
295                 300                 305                 310 agg atg cgt ctt gaa gct agt aaa ctc aat gaa agt gta atg gtt ttt       1014
Arg Met Arg Leu Glu Ala Ser Lys Leu Asn Glu Ser Val Met Val Phe
                315                 320                 325 aca aag gac caa aca gaa aag gaa ata gat gaa atc cac agt aaa tat       1062
Thr Lys Asp Gln Thr Glu Lys Glu Ile Asp Glu Ile His Ser Lys Tyr
            330                 335                 340 cgt aaa aaa cat aag agt gaa ttt cag ctt ctg gtg gat cag gct aga       1110
Arg Lys Lys His Lys Ser Glu Phe Gln Leu Leu Val Asp Gln Ala Arg
        345                 350                 355 aaa gga tac aag aaa att gct gga atg tca caa aaa aca gta aca ata       1158
Lys Gly Tyr Lys Lys Ile Ala Gly Met Ser Gln Lys Thr Val Thr Ile
    360                 365                 370 aca aaa gaa gat gaa tct aca gaa aag cta tct tct gta tgc atg gga       1206
Thr Lys Glu Asp Glu Ser Thr Glu Lys Leu Ser Ser Val Cys Met Gly
375                 380                 385                 390 cag gaa gat aat atg acc tca gta aca aac cac ttt tct caa tca aag       1254
Gln Glu Asp Asn Met Thr Ser Val Thr Asn His Phe Ser Gln Ser Lys
                395                 400                 405 ctg gac tcc cca gag gaa ttg gaa cct gac aga gaa gag gat tct tct       1302
Leu Asp Ser Pro Glu Glu Leu Glu Pro Asp Arg Glu Glu Asp Ser Ser
            410                 415                 420 agc tgt att gat att caa gaa gtt ctt tct tca gaa tca gat tca       1350
Ser Cys Ile Asp Ile Gln Glu Val Leu Ser Ser Glu Ser Asp Ser
        425                 430                 435 tgc aat agt tcc agt tca gac atc ata aga gat ctt tta gaa gaa gag       1398
Cys Asn Ser Ser Ser Ser Asp Ile Ile Arg Asp Leu Leu Glu Glu Glu
    440                 445                 450 gaa gcc tgg gaa gca tca cat aaa aac gat ctt caa gac aca gaa ata       1446
Glu Ala Trp Glu Ala Ser His Lys Asn Asp Leu Gln Asp Thr Glu Ile
455                 460                 465                 470 agt cca aga cag aat cgc cgc aca aga gcc gct gaa agt gct gag att       1494
Ser Pro Arg Gln Asn Arg Arg Thr Arg Ala Ala Glu Ser Ala Glu Ile
                475                 480                 485 gaa cca aga aac aag cgt aat agg aat taa tgtgggcttt tgctgacttt        1544
Glu Pro Arg Asn Lys Arg Asn Arg Asn
            490                 495 tcaaatgcat tgattagaat accgtacttt tggttgccac agatagattt tctatttata    1604
```

```
aatgcccaag gaaagatgct aaattctaaa tattacggtt agctgataaa aaaaaaaaaa    1664
aaaaa                                                                1669
```

<210> SEQ ID NO 2
<211> LENGTH: 495
<212> TYPE: PRT
<213> ORGANISM: Homo sapiens

<400> SEQUENCE: 2

```
Met Asp Ser Leu Ala Glu Ser Arg Trp Pro Pro Gly Leu Ala Val Met
1               5                   10                  15

Lys Thr Ile Asp Asp Leu Leu Arg Cys Gly Ile Cys Phe Glu Tyr Phe
            20                  25                  30

Asn Ile Ala Met Ile Ile Pro Gln Cys Ser His Asn Tyr Cys Ser Leu
        35                  40                  45

Cys Ile Arg Lys Phe Leu Ser Tyr Lys Thr Gln Cys Pro Thr Cys Cys
    50                  55                  60

Val Thr Val Thr Glu Pro Asp Leu Lys Asn Asn Arg Ile Leu Asp Glu
65                  70                  75                  80

Leu Val Lys Ser Leu Asn Phe Ala Arg Asn His Leu Leu Gln Phe Ala
                85                  90                  95

Leu Glu Ser Pro Ala Lys Ser Pro Ala Ser Ser Ser Lys Asn Leu
            100                 105                 110

Ala Val Lys Val Tyr Thr Pro Val Ala Ser Arg Gln Ser Leu Lys Gln
        115                 120                 125

Gly Ser Arg Leu Met Asp Asn Phe Leu Ile Arg Glu Met Ser Gly Ser
    130                 135                 140

Thr Ser Glu Leu Leu Ile Lys Glu Asn Lys Ser Lys Phe Ser Pro Gln
145                 150                 155                 160

Lys Glu Ala Ser Pro Ala Ala Lys Thr Lys Glu Thr Arg Ser Val Glu
                165                 170                 175

Glu Ile Ala Pro Asp Pro Ser Glu Ala Lys Arg Pro Glu Pro Pro Ser
            180                 185                 190

Thr Ser Thr Leu Lys Gln Val Thr Lys Val Asp Cys Pro Val Cys Gly
        195                 200                 205

Val Asn Ile Pro Glu Ser His Ile Asn Lys His Leu Asp Ser Cys Leu
    210                 215                 220

Ser Arg Glu Glu Lys Lys Glu Ser Leu Arg Ser Ser Val His Lys Arg
225                 230                 235                 240

Lys Pro Leu Pro Lys Thr Val Tyr Asn Leu Leu Ser Asp Arg Asp Leu
                245                 250                 255

Lys Lys Lys Leu Lys Glu His Gly Leu Ser Ile Gln Gly Asn Lys Gln
            260                 265                 270

Gln Leu Ile Lys Arg His Gln Glu Phe Val His Met Tyr Asn Ala Gln
        275                 280                 285

Cys Asp Ala Leu His Pro Lys Ser Ala Ala Glu Ile Val Gln Glu Ile
    290                 295                 300

Glu Asn Ile Glu Lys Thr Arg Met Arg Leu Glu Ala Ser Lys Leu Asn
305                 310                 315                 320

Glu Ser Val Met Val Phe Thr Lys Asp Gln Thr Glu Lys Glu Ile Asp
                325                 330                 335

Glu Ile His Ser Lys Tyr Arg Lys Lys His Lys Ser Glu Phe Gln Leu
            340                 345                 350
```

-continued

| | | | | | | | | | | | |
|---|---|---|---|---|---|---|---|---|---|---|---|
|Leu|Val|Asp|Gln|Ala|Arg|Lys|Gly|Tyr|Lys|Lys|Ile|Ala|Gly|Met|Ser|
| | |355| | | |360| | | |365| | | | | |
|Gln|Lys|Thr|Val|Thr|Ile|Thr|Lys|Glu|Asp|Glu|Ser|Thr|Glu|Lys|Leu|
| |370| | | | |375| | | |380| | | | | |
|Ser|Ser|Val|Cys|Met|Gly|Gln|Glu|Asp|Asn|Met|Thr|Ser|Val|Thr|Asn|
|385| | | | |390| | | | |395| | | | |400|
|His|Phe|Ser|Gln|Ser|Lys|Leu|Asp|Ser|Pro|Glu|Glu|Leu|Glu|Pro|Asp|
| | | | |405| | | | |410| | | | |415| |
|Arg|Glu|Glu|Asp|Ser|Ser|Ser|Cys|Ile|Asp|Ile|Gln|Glu|Val|Leu|Ser|
| | | |420| | | | |425| | | | |430| | |
|Ser|Ser|Glu|Ser|Asp|Ser|Cys|Asn|Ser|Ser|Ser|Ser|Asp|Ile|Ile|Arg|
| | |435| | | | |440| | | | |445| | | |
|Asp|Leu|Leu|Glu|Glu|Glu|Ala|Trp|Glu|Ala|Ser|His|Lys|Asn|Asp|
| |450| | | | |455| | | | |460| | | | |
|Leu|Gln|Asp|Thr|Glu|Ile|Ser|Pro|Arg|Gln|Asn|Arg|Arg|Thr|Arg|Ala|
|465| | | | |470| | | | |475| | | | |480|
|Ala|Glu|Ser|Ala|Glu|Ile|Glu|Pro|Arg|Asn|Lys|Arg|Asn|Arg|Asn|
| | | | |485| | | | |490| | | | |495| |

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gaggauucuu cuagcugua                                                    19

USE OF RAD18 INHIBITORS IN THE TREATMENT OF TUMORS

CROSS-REFERENCE TO RELATED APPLICATIONS

The present application is a continuation of U.S. patent application Ser. No. 15/536,437, filed on Jun. 15, 2017, which is the National Stage of International Application No. PCT/EP2015/080883, filed on Dec. 21, 2015, which claims the benefit of European Application No. 14307151.2, filed on Dec. 23, 2014. The contents of all three applications are hereby incorporated by reference in their entirety.

BACKGROUND OF THE INVENTION

The present invention relates to the use of an inhibitor of Rad18 expression or activity, in treating a tumor that is resistant to a treatment with a DNA damaging antineoplastic agent, by sensitization of cancer cells resistant to the said treatment and/or by eradicating cancer stem cells of the said tumor. More particularly, the invention is based on reducing self-renewal of cancer stem cells through targeting Rad18.

Treatment of cancer is mainly based on the use of DNA damaging agents that generate DNA lesions. The mechanism of action of this treatment is to produce a large amount of DNA damage that cannot be efficiently repaired by the tumor cells so as to fully boost a programmed cell death pathway, such as apoptosis, mainly mediated by the genome surveillance mechanisms (checkpoints). ATR, ATM, Chk1, and Chk2 protein kinases comprise main regulators of this signaling pathway (Ciccia and Elledge, 2010).

These kinases in turn phosphorylate a large number of substrates, among which the tumor suppressor protein p53, leading to slowdown of cell proliferation and activation of DNA repair. This signaling pathway is also responsible for activation of programmed cell death pathways (apoptosis, senescence) when the amount of DNA damage is too high. This signaling pathway is currently considered as the main barrier to anarchic proliferation and tumor aggressiveness since genes controlling the checkpoint are found mutated in cancer at malignant stage (Bartkova et al, 2005; Gorgoulis et al, 2005).

However certain tumors are resistant from the start to therapy and manage to escape from the treatment. The mechanism of acquired resistance is completely unknown. This constitutes a major challenge in the actual treatment of cancers.

To date there are no available efficient tools to fight against the acquired resistance of cancer to the therapy which is responsible for cancer recurrence. The resistance to the therapy is incredibly constant, likely underlining a very efficient mechanism of resistance to DNA damage.

Cancerous stem cells, also designated as "tumor initiating cells" (Singh et al, 2003) are currently considered as responsible for the resistance to the therapy. These cells are characterized by self-renewing, multipotency (ability to generate differentiated cells of various types), and tumorogenicity. One example of cancer stem cells resistant to the therapy are those derived from glioblastoma. These cells, and not standard glioblastoma cell lines, such as the U87 cell line, are widely believed to be the more appropriate model system to study glioblastoma since they faithfully reproduce the disease when injected in vivo (Lee et al, 2006). Glioblastoma is the more aggressive and more frequent form of primitive brain tumors. Standard-of-care is surgical resection if possible, followed by the so-named "Stupp" protocol (Stupp et al, 2009), a therapy that involves a combination of ionizing radiations with temozolomide, an alkylating agent. Despite this heavy treatment, the mean survival of patients with glioblastoma is shorter than 16 months.

SUMMARY OF THE INVENTION

The inventors have now demonstrated, that Rad18 is a specific marker of cancer stem cells. They propose to use inhibitors of Rad18 expression or activity to limit the self-renewal of cancer stem cells and decrease the growth of such cells as well as render the tumor cells sensitive to a treatment with DNA damaging agents.

The present invention relates to the use of an inhibitor of Rad18 expression or activity, in treating a tumor or in sensitizing a patient affected with a tumor, to a treatment with an antineoplastic agent that is a DNA damaging chemotherapeutic agent so to both reduce the self renewal of cancer stem cells and increase the DNA damage response thus boosting apoptotic cell death.

The present invention provides an inhibitor of Rad18 expression or activity, for use in treating a tumor that is resistant to a treatment with a DNA damaging antineoplastic agent, in a patient.

In a first aspect, the tumor is a tumor that comprises cancer stem cells. The inhibitor advantageously kills said cancer stem cells, reduces self renewal of said cells and/or decreases the growth of said cells.

An inhibitor of Rad18 expression or activity is particularly useful in reducing the risk of cancer relapse in the patient.

In a second aspect, the inhibitor is used in sensitizing a patient affected with a tumor that is resistant to a treatment with a DNA damaging antineoplastic agent, wherein the tumor becomes sensitive to said antineoplastic agent.

It is further provided a method for treating a tumor in a patient, which method comprises administering the patient with an inhibitor of Rad18 expression or activity, before administering the patient with an antineoplastic agent that is a DNA damaging chemotherapeutic agent. The inhibitor of Rad18 expression or activity sensitizes the patient to the subsequent administration of the antineoplastic agent.

This method for sensitizing a patient affected with a tumor, toward a treatment with a DNA damaging antineoplastic agent, is particularly useful in treating tumors resistant to such a treatment, more particularly in tumors whose resistance is attributed to cancer stem cells.

In a further aspect, it is provided an inhibitor of Rad18 expression or activity, for use in treating a tumor in a patient, or for reducing the risk of cancer relapse, wherein the tumor is preferably a tumor that comprises cancer stem cells. In this embodiment the inhibitor of Rad18 expression or activity may be used in monotherapy, as a sole antitumor agent. The inhibitor hereby reduces self renewal of cancer stem cells and/or decreases the growth of said cells.

It is thus described a method for treating a tumor in a patient, or reducing the risk of cancer relapse, which method comprises administering the patient with an inhibitor of Rad18 expression or activity.

It is further described a method for killing or eradicating cancer stem cells in a patient, which method comprises administering the patient with an inhibitor of Rad18 expression or activity.

The invention further provides a method for determining whether a patient treated for a tumor is at risk of a cancer relapse, which method comprises determining the expression level of Rad18 in a biological sample of the patient, preferably a tumor sample, wherein a higher expression compared to a control is indicative of the presence of cancer stem cells which are likely to develop and cause a cancer relapse.

The invention also provides a method for monitoring efficacy of an anti-tumor treatment in a patient affected with a tumor which comprises cancer stem cells, which method comprises determining the expression level of Rad18 in the tumor or in a biological sample of the patient, preferably a tumor sample, wherein a higher expression compared to a control is indicative of the presence of residual cancer stem cells.

LEGENDS TO THE FIGURES

FIG. 1. Inhibition of replication fork uncoupling at low N/E ratio (A) Egg extracts supplemented with sperm nuclei at low (100 nuclei/μl) or high (1000 nuclei/μl) N/E ratio, UV-irradiated (+UV) or not (−UV), were incubated at room temperature for 50 minutes. Nuclei were isolated, chromatin-bound proteins were eluted with Laemmli buffer and analyzed by western blot following SDS-PAGE with the indicated antibodies.

(B) Cartoon showing titration of a putative maternally-supplied factor (brown circles) on chromatin by the increase in nuclei number (circles) at increased N/E ratio.

(C) Comparison of abundance of the indicated proteins remaining in egg extracts after incubation with sperm nuclei at low or high N/E ratio. Egg extracts were supplemented with either 100 (low N/E ratio) or 1000 (high N/E ratio) nuclei/μl and incubated at room temperature for 90 minutes. Cytoplasmic fractions (Unbound), or chromatin-bound fractions were recovered and analyzed by western blot with the indicated antibodies.

(D) Comparison of abundance of the indicated proteins of the experiment of panel c on chromatin after incubation with sperm nuclei at low or high N/E ratio. Chromatin-bound fractions were recovered and analyzed by western blot with the indicated antibodies.

(E) Rad18 interacts with Drf1 at low N/E ratio in egg extracts. Western blot of Rad18 immunoprecipitates obtained from *Xenopus* egg extracts after nuclear assembly at low or high N/E ratio. Low (light) and high (dark) exposures of Drf1 are shown. Complex formation is observed at low N/E ratio while this complex is barely detectable at high N/E ratio.

Figure 2:
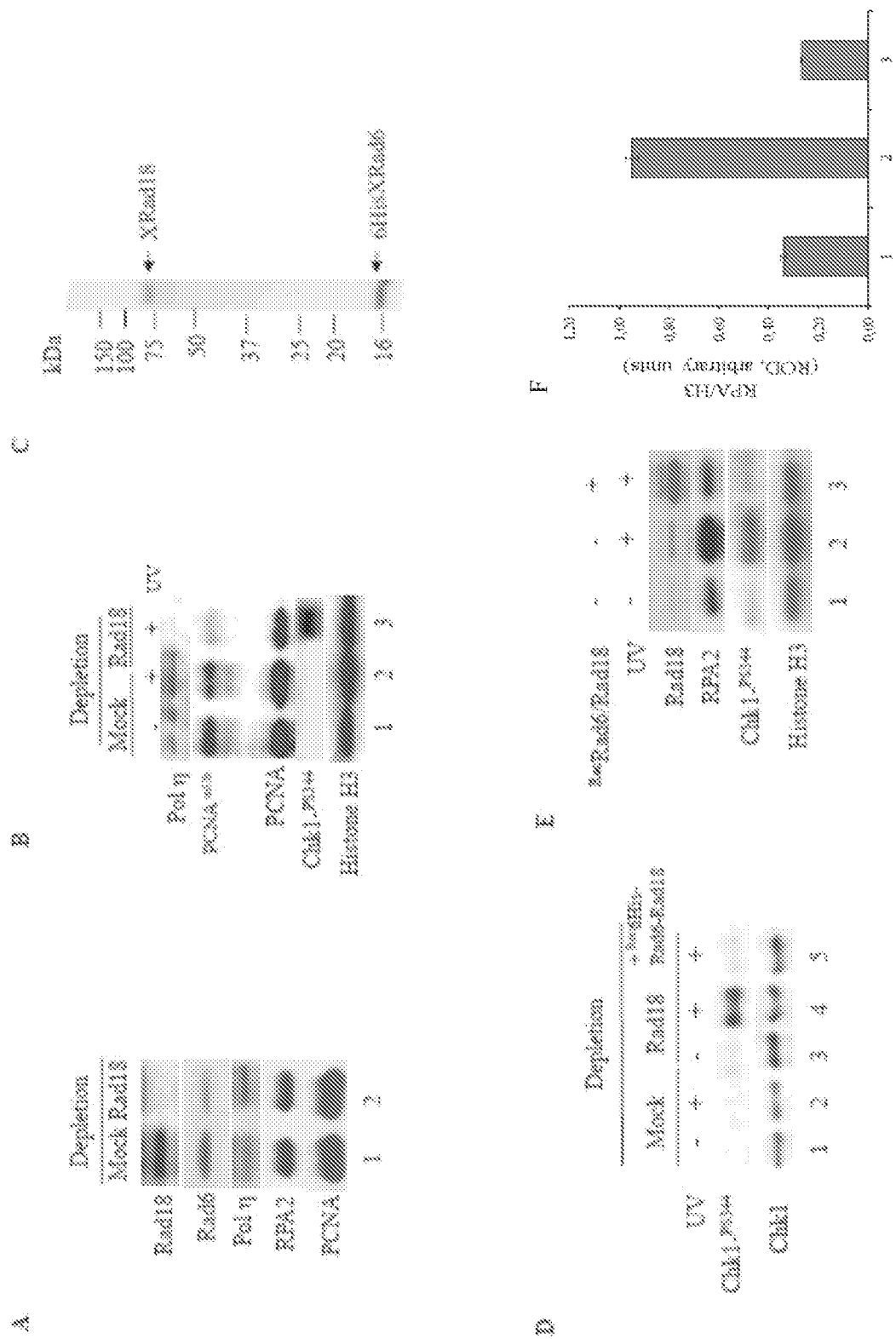

FIG. 2. Depletion of Rad18 from egg extracts stimulates Chk1 phosphorylation at low N/E ratio upon UV damage (A-B) Egg extracts (A) or chromatin (B) UV irradiated (+) or not (−), obtained at low N/E ratio upon depletion with non-specific antibodies (Mock) or Rad18-specific antibodies, were analyzed by western blot with the indicated antibodies.

(C) Coomassie blue staining of the recombinant 6His-rad6-Rad18 complex expressed and purified from insect cells. kDa indicates molecular weight of standard proteins markers.

(D) Either mock-depleted, or Rad18-depleted egg extracts were reconstituted with UV-irradiated (+UV) or not (−UV) sperm nuclei at low N/E ratio, as well as with the recombinant (Rec) 6His-Rad6-Rad18. Chk1 phosphorylation was analyzed by western blot with phospho-specific antibodies. Chk1 serves as loading control. Egg extracts immunodepleted of Rad18 with the Rad18 antibody.

(E) Inhibition of RPA hyperloading on UV-irradiated chromatin at high N/E ratio. Recombinant 6His-Rad6-Rad18 was added to egg extracts in the presence of UV-irradiated sperm chromatin at high N/E ratio. Reactions were incubated at room temperature for 60 minutes. Chromatin fractions were analyzed for the binding of Rad18 and RPA2 in the absence (−) or presence (+) of UV-irradiated sperm nuclei.

(F) Quantification of RPA2 accumulation upon addition of exogenous recombinant 6His-Rad6-Rad18, described in panel E, normalized to Histone H3. Numbers indicated lanes of panel E. ROD: Relative Optical Density. Means and standard deviation are shown.

Figure 3:
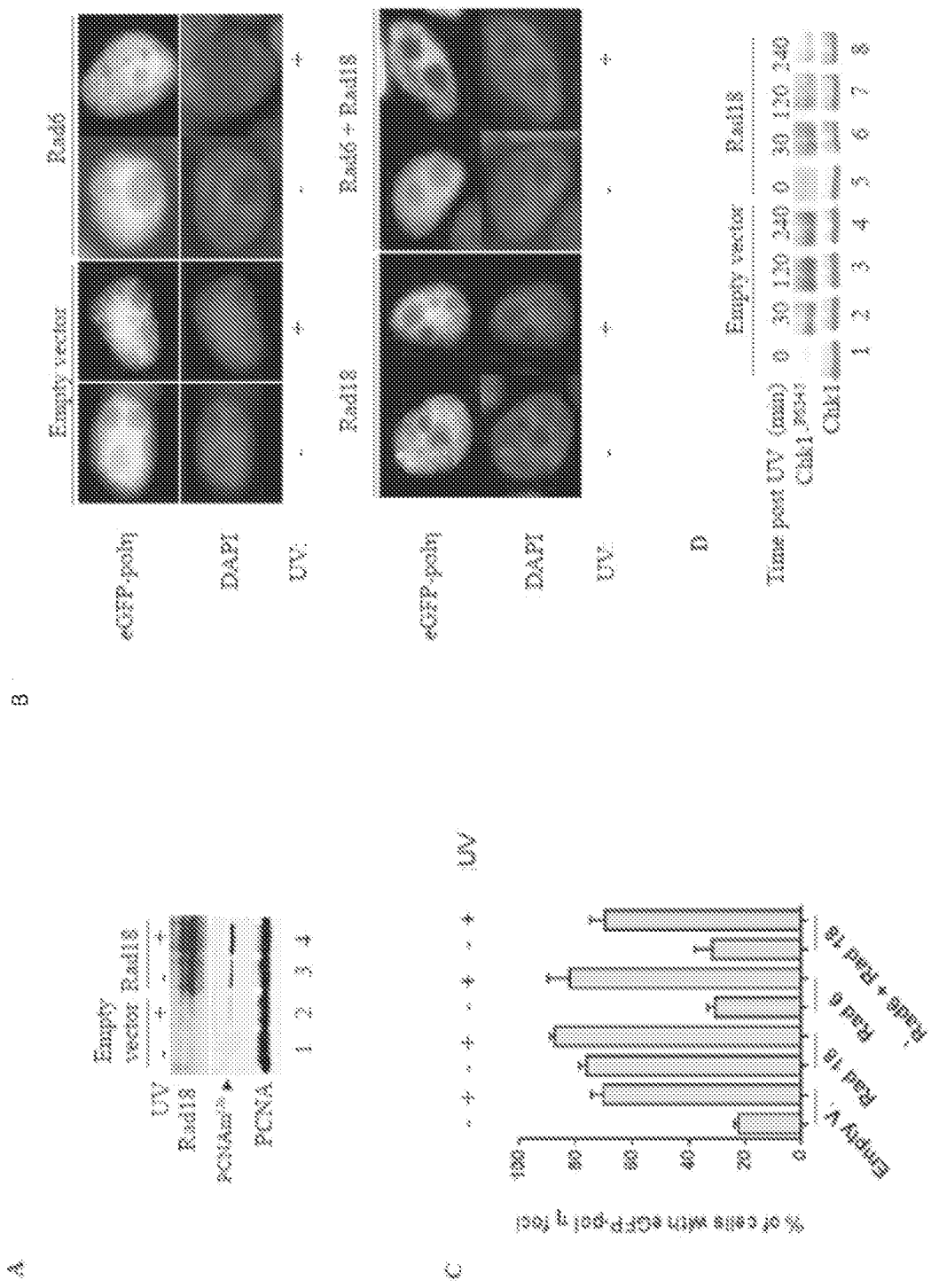

FIG. 3. Ectopic Rad18 expression induces spontaneous formation of TLS Polη foci and suppresses UV-dependent Chk1 phosphorylation in mammalian cells (A) HEK293T cells were transfected with Rad18 under control of the CMV promoter or empty vector (pCDNA3). Twenty-four hours later total cell extracts were obtained as described above and analyzed by western blot with the indicated antibodies.

(B) Expression of Rad18, and not Rad6, in mammalian HEK293T cells induces constitutive formation of Polη foci. Cells transfected with the indicated expression vectors and eGFP-Polη were stained with DAPI to visualize DNA and observed for eGFP fluorescence.

(C) Quantification of eGFP-Polη foci from the experiment described in panel B. Means and standard deviation of three independent experiments are shown.

Figure 4:
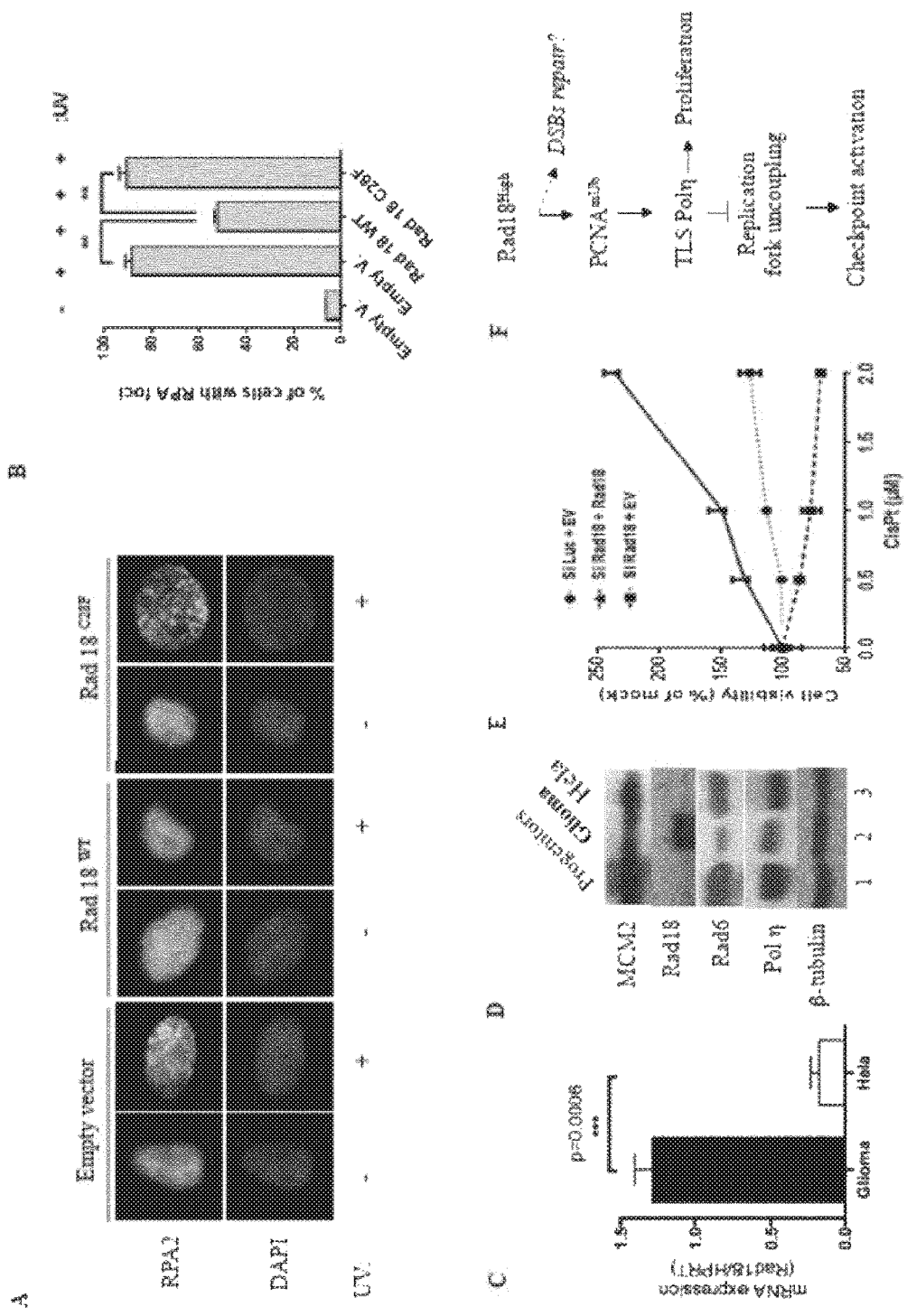

(D) Determination of Chk1S345 phosphorylation in HEK293T cells expressing empty vector or Rad18, in the presence of UV irradiation (+UV) at the indicated times FIG. 4. Ectopic Rad18 expression and resistance to DNA damage (A) Expression of Rad18, suppresses formation of RPA foci upon UV irradiation in mammalian cells. HEK293T cells transfected with the indicated expression vectors (efficiency of transfection 70%) and UV-irradiated. Cells were stained with DAPI to visualize DNA, and RPA2 antibodies as read out for formation of ssDNA by fluorescence microscopy.

(B) Quantification of RPA2 foci from the experiment described in panel A. Means and standard deviation are shown (**p<0.01).

(C) Expression of Rad18 mRNA in gliospheres (CD133+, gliomes) compared to Hela cells using primer pair specific for the human Rad18 gene. Means and standard deviation of three independent experiments are shown.

(D) Western blot of total cell extracts prepared from glioblastoma biopsies (glioma, grade 4) differentiated counterparts (progenitors, CD133−) or Hela cells.

(E) Survival curves of U87 glioblastoma cells co-transfected with empty vector and non-specific siRNA (siLuc+EV), or Rad18-specific siRNA and empty vector (siRad18+EV) and rescued by co-transfection with Rad18 (siRad18+Rad18), challenged with the indicated doses of cisplatin (CisPt) normalized to non-treated cells (mock). Means and standard deviations are shown (n=3).

(F) Schematic representation of Rad18 function in checkpoint signaling. High Rad18 expression inhibits replication fork uncoupling thus shunting checkpoint activation and stimulating cell proliferation in the presence of DNA damage. High Rad18 expression may also enhance the ability to repair DNA double strand breaks (DSBs).

Figure 5:
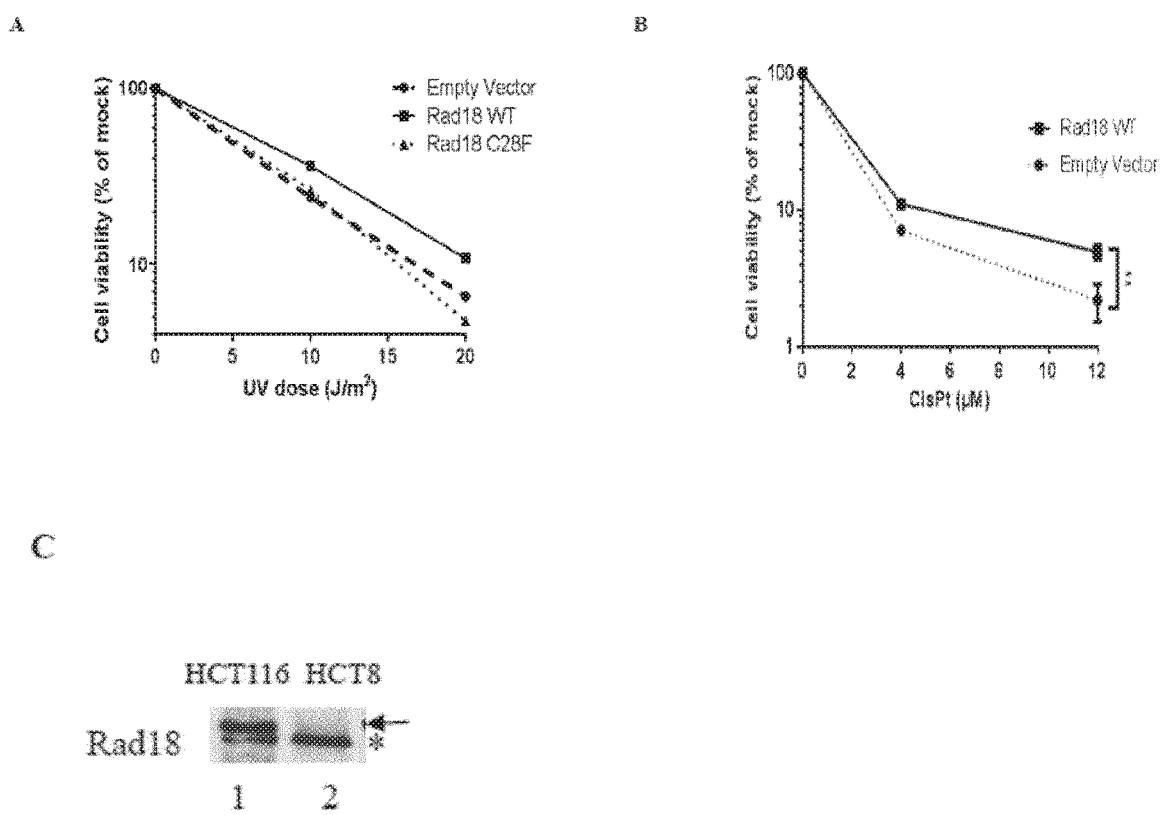

FIG. 5. High Rad18 expression in DNA damage-resistant cancer cell lines (A-B) Survival curves of asynchronous NIH3T3 cells stably expressing either empty vector, low levels of Rad18 wild-type or C28F Rad18 mutant, challenged by the indicated doses of UV-C (A) or cisplatin (CisPt, B) normalized to non-irradiated cells (mock). Means and standard deviations are shown (n=3).

(C) Expression of Rad18 in HCT-116 and HCT-8 colorectal cancer cell lines respectively resistant or sensitive to oxaliplatin treatment (2). Asterisk indicates a non-specific crossreacting polypeptide.

Figure 6:
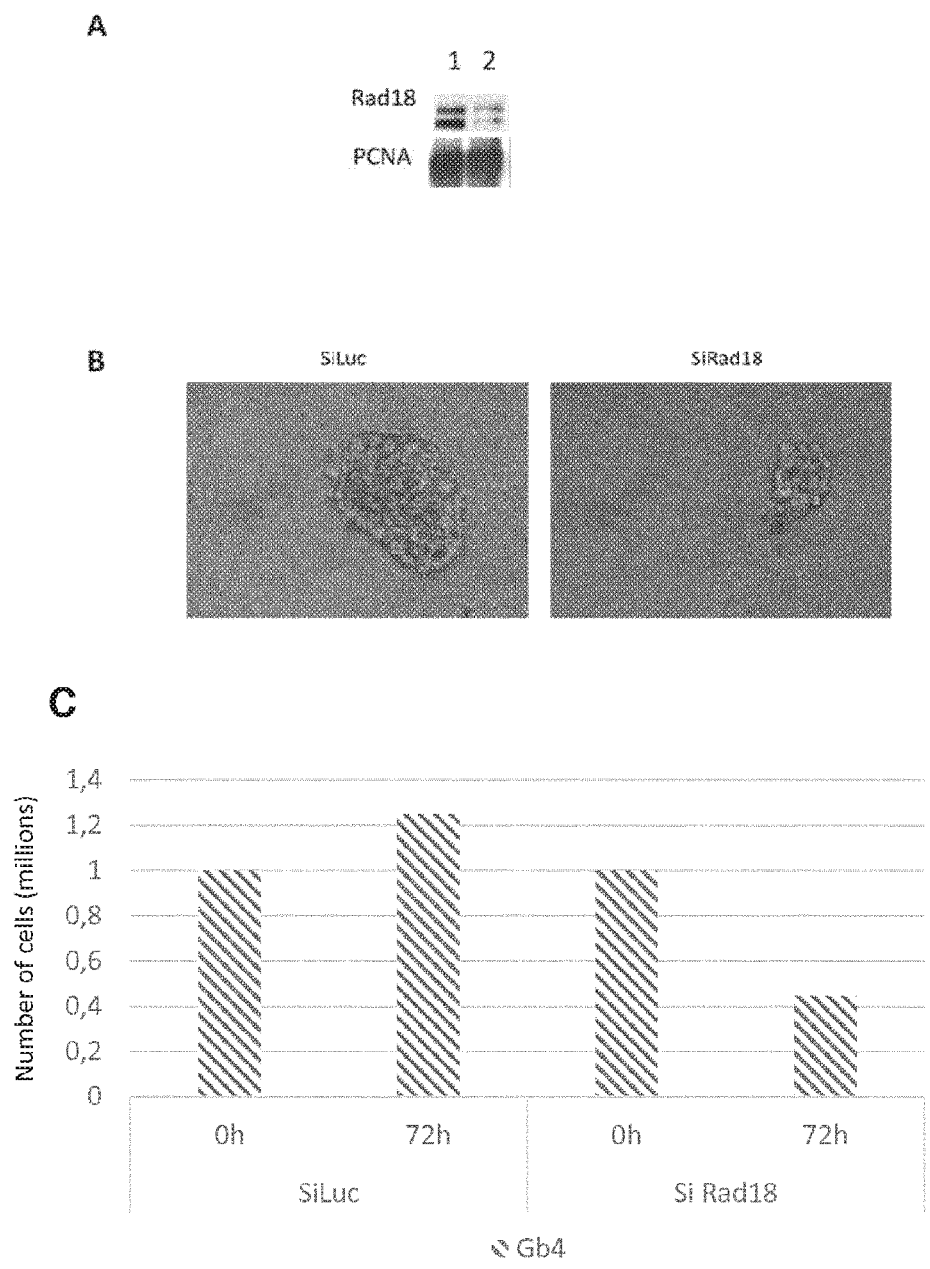

FIG. 6. Rad18 downregulation affects the proliferation of glioblastoma cancer stem cells in the absence of external damage. (A) Western blot of Gb4 glioblastoma cancer stem cells extracts treated with control siRNA (siLuc, lane 1), or a Rad18-specific siRNA (siRad18, lane 2) analysed 72 hours post-treatment. Extracts were probed with anti-Rad18 or anti-PCNA antibodies. (B) Phase contrast microscopy images of gliospheres treated with control siRNA or Rad18-specific siRNA 72 hours post-treatment. (C) Quantification of gliospheres proliferation upon downregulation of Rad18 expression expressed as number of cells. Glioblastoma cancer stem cells extracts were treated as described in panel A and cells were counted before (0 h) or 72 hours post-treatment (72 h).

Figure 7:
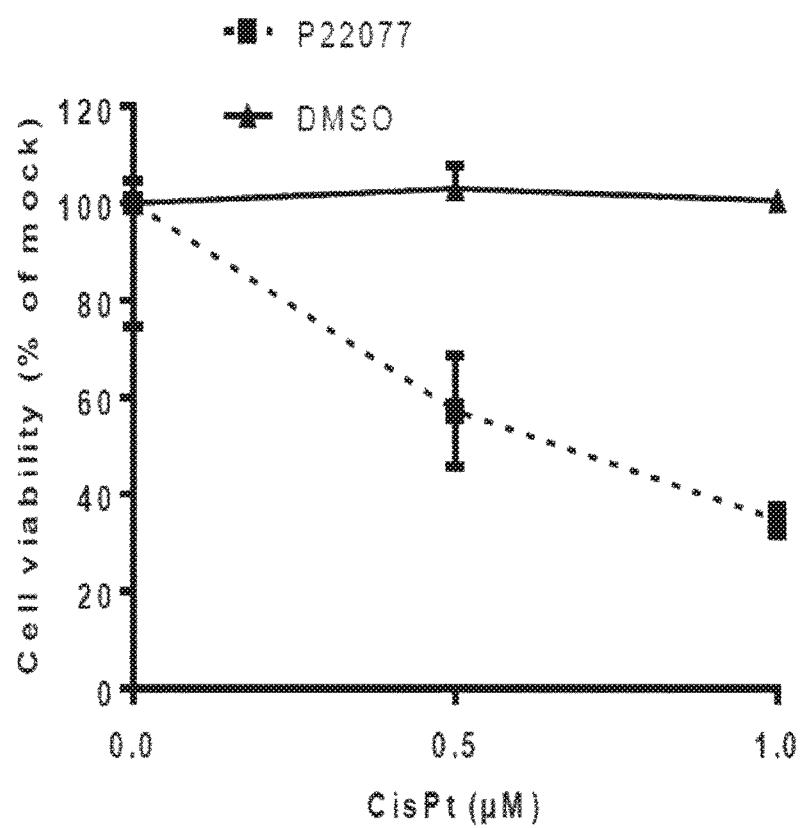

FIG. 7. The USP7 inhibitor P2207 sensitizes glioblastoma to cisplatin treatment. Survival curves of U87-MG glioblastoma cells treated with the indicated doses of the USP7 inhibitor P2207 (Sigma-Aldrich), or DMSO as a control. Means and standard deviations are shown (n=3). Cell viability is expressed as percent (%) of viability compared to the control (DMSO).

DETAILED DESCRIPTION OF THE INVENTION

Definitions

The term "cancer stem cells" (CSCs), or "tumor initiating cells" refer to cancer cells (found within solid tumors or hematological cancers) that possess characteristics associated with normal stem cells, specifically the ability to give rise to all cell types found in a particular cancer sample. CSCs are therefore tumorigenic (tumor-forming). CSCs are CD133+ cells. CSCs may generate tumors through the stem cell processes of self-renewal and differentiation into multiple cell types. Such cells are proposed to persist in tumors as a distinct population and cause relapse and metastasis by giving rise to new tumors. Cancer stem cells are also capable of resurrection after morphological and biochemical apoptosis.

The "subject" or "patient" to be treated may be an animal such as a mammal. Preferably, the subject to be treated is human. The subject may be an infant, a child, an adult or an elder. The subject has been previously diagnosed as having cancer, and possibly has already undergone treatment for the cancer.

The term "treating" means any improvement in the cancer status of the patient, e.g. increasing life expectancy in a patient affected with the cancer, or alleviating at least one symptom, or stopping or slowing down the progression of the disease, or reducing the risk of relapse or of metastasis.

A patient, a tumor, or a tumor cell, that is "sensitive" to a treatment, is a patient, tumor or tumor cell that positively responds to said treatment. Conversely, a patient, tumor or tumor cell that is "resistant" to a therapy or treatment is a patient, tumor or tumor cell that does not respond, or does not substantially respond to said therapy or treatment.

The term "sensitizing" herein means that a patient, tumor or tumor cell is rendered sensitive to a treatment, or that its sensitivity to a treatment is increased.

The term "reducing" or "inhibiting" self-renewal of cancer stem cells means that the capacity of proliferation of cancer stem cells is diminished by at least 30%, preferably at least 40%, 50%, 60%, 70%, or 80%.

Tumors:

In the context of the present invention, the term "tumor" means malignant tumor, or cancer. The method encompasses treating any solid tumor or hematological cancer. Solid tumors are preferred.

Tumors known for their resistance to DNA damaging antineoplastic agents are more particularly encompassed, especially tumors whose resistance is attributed to cancer stem cells. Cancers of embryonic origin or those generated by dedifferentiation of somatic cells are more particularly included.

According to the invention, the tumor that is resistant to a treatment with said antineoplastic agent becomes sensitive to said antineoplastic agent.

According to the invention, inhibition of Rad18 expression or activity will further result in inhibiting self-renewal of cancer stem cells.

Typical examples of tumors that may benefit from the invention include brain cancer such as gliomas, especially glioblastoma, as well as colorectal carcinoma, lung cancer, e.g. non-small cell lung, breast cancer, ovarian cancer, or leukemia.

Pancreas cancer, esophageal cancer, prostate cancer, melanoma, multiple myeloma, non-melanoma skin cancers are also encompassed.

Rad18 Inhibitors:

The invention involves administration of an inhibitor of Rad18 expression or activity.

RAD18, also called E3 ubiquitin-protein ligase RAD18, is a human enzyme that is involved in the translesion DNA synthesis (TLS). It is encoded by the Rad18 gene. This gene has been mapped on chromosome 3 of the human genome. The cDNA sequence (SEQ ID NO: 1) and the amino acid sequence (SEQ ID NO:2) of human RAD18 are available on Genebank Access Number AY004333.1.

In a first embodiment, the invention makes use of an inhibitor of Rad18 expression.

Such inhibition, or "gene silencing", refers to a process by which the expression of Rad18 gene product is lessened or attenuated. The level of Rad18 inhibition or gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Blot Analysis, measuring the levels of expression of a reporter protein that has e.g., fluorescent properties (e.g., GFP) or enzymatic activity (e.g., alkaline phosphatases), or several other procedures.

Such inhibition can take place by a variety of pathways, especially by RNA interference. In a particular embodiment, the inhibitor of Rad18 expression is a nucleic acid that inhibits the expression of Rad18.

Various means for RNA interference may be used. In the context of the present invention, the inhibitor of Rad18 expression is preferably a nucleic acid that inhibits the expression of Rad18 and is selected from the group consisting of small interfering RNA (siRNA), small hairpin RNA (shRNA), micro RNA (miRNA), an aptamer, a ribozyme, and an antisense oligonucleotide.

Preferred molecules capable of mediating RNA interference advantageously down regulate at least 50%, preferably at least 60%, preferably at least 70%, preferably at least 80%, even more preferably at least 90%, of the target protein expression.

The term "siRNA" refers to small inhibitory RNA duplexes that induce the RNAi pathway. As mentioned above, these molecules can vary in length, with each strand being 18-30 or 18-25 or 18-23 or 19-23 nucleotides long and can contain varying degrees of complementarity, e.g., at least 80 percent, at least 90 percent or 100 percent between the antisense and sense strands (independent of any overhangs that may or may not exist) and between the antisense strand (independent of any overhangs that may or may not exist) and its target mRNA.

An example of siRNA that inhibits Rad18 expression shows sequence GAG GAU UCU UCU AGC UGU A (SEQ ID NO:3).

A "shRNA" is a small hairpin RNA. It is a single strand of RNA that contains a hairpin turn and that can be used to silence RNA via RNAi. Each shRNA typically contains an antisense region and a sense region that are to varying degrees complementary to each other, as well as a sequence between them that enables formation of a loop structure. Thus, the stem (including the antisense and sense regions and any additional bases prior to the formation of the loop) may be 18 to 35 base pairs long and the loop may be 4 to 15 bases long. The antisense region and the sense region of a shRNA are typically defined in the same way that the antisense and sense strands are defined for an siRNA, including but not limited to by length and degree of complementarity.

It is known that siRNAs with a sequence composed of 30 to 50% of guanines and cytosines are more effective than sequences with a higher proportion of guanines and cytosines. Therefore the siRNAs used in the invention advantageously have a sequence composed of 30 to 50% of guanines and cytosines.

It should be understood that a siRNA can equally comprise two complementary single stranded RNA molecules, or a single stranded RNA molecule in which two complementary portions are paired by Watson-Crick bonds and are linked covalently on one side by a hairpin type structure (this is more specifically known as shRNA for "short hairpin RNA"), which can be considered as a subclass of siRNA.

Moreover, the sense and/or antisense RNA strands can further comprise a 3' overhang fragment of 2 to 4 nucleotides, in particular when a siRNA according to the invention comprises two complementary single stranded RNA molecules. The expression "3' overhang fragment of 2 to 4 nucleotides" as used herein is understood to mean the presence in at least one strand of the RNA duplex of 2 to 4 nucleotides not paired with the complementary strand at the 3' distal end of said strand.

Furthermore, in an interferent RNA according to the invention, such as a siRNA or an antisense, the sense RNA strand and/or the antisense RNA strand can also comprise at least one chemical modification in their sugar portions, their nucleobase portions or their internucleotide backbone. Such modifications can notably make it possible to inhibit the breakdown of siRNAs by nucleases in vivo. All chemical modifications that enable the improvement of the stability and in vivo bioavailability of siRNAs are thus included in the scope of the invention.

An "antisense RNA" is a single stranded RNA molecule that is at least 80 percent, at least 90 percent or 100 percent complementary to a region of a messenger RNA. In some embodiments, it is 50 to 500 nucleotides in length.

A micro RNA ("miRNA") is a small non-coding RNA molecule that functions in transcriptional and post-transcriptional regulation of gene expression. miRNA mimics may be encompassed, which include but are not limited to MISSION® human miRNA mimics from Sigma-Aldrich, miRIDIAN® microRNA mimics from Thermo Scientific, miScript® miRNA mimics from Qiagen, and mirVana™ mimics from Life Technologies. A mimic may be the same as the miRNA or be at least 80 percent similar, at least 90 percent similar or 100 percent similar to the miRNA.

Methods for synthesizing siRNA are known in the art and for example, are disclosed in Rohn et al., 2012. Methods for synthesizing shRNA or microRNA are known in the art and for example, are disclosed in Hwang do et al., 2011. Generally speaking, an siRNA and antisense nucleic acid capable of specifically inhibiting the expression of Rad18 can be prepared by determining the target sequence on the basis of an mRNA sequence or chromosomal DNA sequence of Rad18, and synthesizing a nucleotide sequence complementary thereto using a commercially available automated DNA/RNA synthesizer (Applied Biosystems, Beckman and the like). The siRNA can be prepared by separately synthesizing a sense strand and an antisense strand using an automated DNA/RNA synthesizer, and denaturing the strands in an appropriate annealing buffer solution at about 90° C. to about 95° C. for about 1 minute, and then performing annealing at about 30° C. to 70° C. for about 1 to about 8 hours. A longer double-stranded polynucleotide can be prepared by synthesizing complementary oligonucleotide strands in a way such that they overlap with each other, annealing the strands, and then performing ligation with a ligase.

The siRNA molecules may be either synthesized or produced by cleavage of corresponding shRNAs by DICER. Such shRNAs can be produced from vectors comprising corresponding nucleic acid sequences.

An "aptamer" is an oligonucleotide or peptide molecule that binds to a specific target molecule. When an aptamer is a peptide, it may contain a short variable peptide domain that is attached at both ends to a protein scaffold. Aptamers can be combined with ribozymes to self-cleave in the presence of a target molecule. As persons of ordinary skill in the art recognize, there are natural aptamers or riboswitches and artificial aptamers.

A "ribozyme" is a ribonucleic acid enzyme. Thus, it is an RNA molecule that is capable of catalyzing specific biochemical reactions. Ribozymes may be naturally occurring or artificial, and they may be capable of self-cleaving or catalyzing the formation of covalent bonds.

In another embodiment, the inhibitor of Rad18 expression is selected from the group consisting of a zinc-finger nuclease (ZFN), a transcription-activator like effector nuclease (TALEN), and a RNA-guided DNA endonuclease. Such techniques of "genome editing" are described e.g. in Gaj et al, 2013.

They are based on the use of engineered nucleases composed of sequence-specific DNA-binding domains fused to a nonspecific DNA cleavage module. These chimeric nucleases enable efficient and precise genetic modifications by inducing targeted DNA double-strand breaks (DSBs) that stimulate the cellular DNA repair mechanisms.

One example of a targeted nuclease that may be used in the subject methods is a zinc finger nuclease or "ZFN". ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion.

Another example of a targeted nuclease that finds use in the subject methods is a TAL Nuclease ("TALN", TAL effector nuclease, or "TALEN"). A TALN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in Christian et al. 2010; and in Li, et al., 2010.

CRISPR interference (CRISPRi) using an engineered CRISPR-Cas system can be used for downregulation of Rad18 gene expression. The CRISPR (clustered regularly interspaced short palindromic repeats) locus comprises short repetitive sequences (30-40 base pairs) separated by short spacer sequences. Transcription at the CRISPR locus results in the production of small CRISPR RNAs that contain full or partial spacer sequences. Endogenous CRISPR RNA-Cas systems comprise a Cas nuclease that is guided to target sites by a complex of two small RNAs, the CRISPR RNA (crRNA), which contains a targeting sequence, and a common trans-activating CRISPR RNA (tracrRNA). See e.g., Richter et al. 2013; Barrangou 2013; Jinek et al. 2013; Larson et al. 2013.

In another embodiment, the inhibitor of Rad18 is an inhibitor of Rad18 activity.

Such inhibitors advantageously down regulate at least 50%, preferably at least 60%, preferably at least 70%, preferably at least 80%, even more preferably at least 90%, of the target protein activity.

Preferably, the inhibitor of Rad18 activity is a direct inhibitor, i.e. it directly interacts with Rad18 protein.

The term "Rad18 activity" herein preferably refers to the enzymatic activity of Rad18 as ubiquitin ligase, which can be measured by any technique known in the art. The action of the inhibitor can be examined by measuring the ubiquitine ligase activity of Rad18 in the presence or absence of an inhibitor. This can be achieved in vitro by testing the ability of Rad18 to catalyze the transfer of an ubiquitin monomer onto the substrate PCNA as described in Watanabe et al., 2004, or in vivo to induce formation of Y-family translesion DNA polymerases (eta, kappa, iota, rev1) foci upon treatment with DNA damaging agents, such as MMS or cisplatin, as described in Kannouche et al., 2004, or to induce formation of 53BP1 foci upon induction of double strand breaks with ionizing radiations or radiomimetic agents, such as doxorubicin, as described in Huang et al., 2009.

Therefore the inhibitor of Rad18 activity is preferably an inhibitor of the ubiquitine ligase activity of Rad18.

In a particular embodiment, the inhibitor of Rad18 activity is a small molecule, ie a chemically synthesized compound (which is not a polymer, therefore excluding nucleic acids and polypeptides) that is capable of interfering with Rad18 activity.

In another embodiment, the inhibitor of Rad18 activity is an anti-Rad18 antibody. The term "anti-Rad18 antibody" refers to an antibody that binds to Rad18 protein, and blocks its activity. Anti-Rad18 neutralizing antibody. Specific antibodies are preferred, i.e. antibodies that show substantially no cross-reaction with any other entity. Preferably the antibody binds Rad18 with a high affinity, e.g. with a Kd of less than about $10^{-9}$.

The term "antibody", as used herein, is intended to refer broadly to any immunologic binding agent such as IgG, IgM, IgA, IgD and IgE, and human, humanized or chimeric antibody. In certain embodiments, IgG and/or IgM are preferred because they are the most common antibodies in the physiological situation and they are most easily manufactured. The term "antibody" is used to refer to any antibody-like molecule that has an antigen binding region, and includes antibody fragments such as Fab', Fab, F(ab') 2, single domain antibodies (DABs), Fv, scFv (single chain Fv), and the like. The techniques for preparing and using various antibody-based constructs and fragments are well known in the art. Means for preparing and characterizing antibodies are also well known in the art. A "humanized" antibody is an antibody in which the constant and variable framework region of one or more human immunoglobulins is fused with the binding region, e.g. the CDR, of an animal immunoglobulin. "Humanized" antibodies contemplated in the present invention are chimeric antibodies from mouse, rat, or other species, bearing human constant and/or variable region domains, bispecific antibodies, recombinant and engineered antibodies and fragments thereof. Such humanized antibodies are designed to maintain the binding specificity of the non-human antibody from which the binding regions are derived, but to avoid an immune reaction against the non-human antibody. A "chimeric" antibody is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In still another embodiment, the inhibitor of Rad18 activity is an inhibitor of Ubiquitine Specific Protease 7 (USP7), such as P22077.

USP7 removes ubiquitin from Rad18. Using an inhibitor of USP7 leads to the destruction of Rad18, being tagged with ubiquitin.

The Antineoplastic Agent

The present invention sensitizes the tumor cells to antineoplastic agents which act as DNA damaging agents.

The cells treated with the inhibitor of Rad18 expression or activity will be particularly impaired in the repair of DNA Double-Strand Breaks and/or translesion DNA synthesis. According to the invention, the inhibitor of Rad18 expression or activity will thus make the DNA damage checkpoint more efficient, whereby the tumor cells become more sensitive to any DNA damage induced by a DNA damaging agent.

Such DNA damaging agents are chemotherapeutic agents which may be selected from the group consisting of a crosslinking agent, such as a platinum compound, a strand break agent, an alkylating agent, an antimetabolite agent, an intercalator, a DNA replication inhibitor, an anthracycline, an etoposide, and a topoisomerase inhibitor.

Preferably, the agent is selected from the group consisting of a platinum compound, an alkylating agent, and a topoisomerase inhibitor.

In a preferred embodiment, the antineoplastic agent is a platinum compound selected from the group consisting of cisplatin, carboplatin, oxaliplatin, arboplatin, nedaplatin, and satraplatin.

In another embodiment, the antineoplastic agent is a topoisomerase inhibitor such as camptothecin. Other useful topoisomerase inhibitors include topoisomerase I inhibitors, e.g. irinotecan, topotecan, and lamellarin D, and topoisomerase II inhibitors, e.g. etoposide (VP-16), teniposide, doxorubicin, daunorubicin, mitoxantrone, amsacrine, ellipticines, or aurintricarboxylic acid.

In still another embodiment, the antineoplastic agent is an alkylating agent, such as methylmethane sulfonate (MMS), cyclophosphamide, mechlorethamine or mustine (HN2), uramustine or uracil mustard, melphalan, chlorambucil, ifosfamide, bendamustine, carmustine, lomustine, streptozocin, busulfan.

Administration of the Rad18 Inhibitor

According to the invention, the inhibitor of Rad18 expression or activity may be administered by any convenient route, especially intravenously or intraperitoneally. It may also be directly administered or injected into the solid tumor.

The pharmaceutical composition comprising the inhibitor is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. The pharmaceutical composition may comprise one or several inhibitors of Rad18 expression or activity. The pharmaceutical composition may also comprise additional active substance(s).

The dosage and route of administration can be determined by any skilled physician, depending on the inhibitor and the severity of the disease. For example, the inhibitor may be administered at a daily dosage of 10 μg to 100 mg, preferably during a period of one to seven days.

It is further provided a method for treating a tumor in a patient, which method comprises administering a Rad18 inhibitor in a patient in need thereof, before administering the patient with a therapeutically effective amount of a DNA damaging antineoplastic agent. According to the invention, the Rad18 inhibitor allows to sensitize the patient to the action of the antineoplastic agent.

Accordingly, in a preferred embodiment, the inhibitor is to be administered within one day to one week before the patient is administered with said antineoplastic agent.

In another embodiment, the inhibitor is administered alone, as a monotherapy for treating cancer or for reducing the risk of relapse.

Rad18 as a Biomarker of Cancer Stem Cells

The invention further provides a method for determining whether a tumor is resistant or, is expected to be resistant, to a therapy with a DNA damaging antineoplastic agent, which method comprises determining the expression level of Rad18 in the tumor, wherein a higher expression compared to a control, such as a non-cancerous tissue neighboring the tumor, is indicative of the presence of cancer stem cells which are resistant to a therapy with a DNA damaging antineoplastic agent. Typically the method is performed in vitro, on a tumor sample.

If so, the patient may then be treated with an inhibitor of Rad18 expression or activity, in order to upregulate the DNA damage checkpoint response and increase tumor cell death.

The invention further provides a method for determining whether a patient treated for a tumor is at risk of a cancer relapse, which method comprises determining the expression level of Rad18 in the tumor or a biological sample of the patient, preferably a tumor sample, wherein a higher expression compared to a control is indicative of the presence of cancer stem cells which are likely to develop and cause a cancer relapse.

The invention also provides a method for monitoring efficacy of an anti-tumor treatment in a patient affected with a tumor which comprises cancer stem cells, which method comprises determining the expression level of Rad18 in the tumor or a biological sample of the patient, preferably a tumor sample, wherein a higher expression compared to a control is indicative of the presence of residual cancer stem cells.

The "residual" cancer stem cells are cancer stem cells which have not been eradicated by the anti-tumor treatment. This is particularly useful for monitoring efficacy of a treatment with a chemotherapeutic agent, such as a DNA damaging antineoplastic agent.

The above methods are typically performed in vitro. Alternatively they may be performed in situ.

The expression level of Rad18 in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), Taqman probes, RNA-Seq, FISH (fluorescence in situ hybridization), microarray analysis, gene expression profiling, and/or serial analysis of gene expression ("SAGE"), as well as any one of the wide variety of assays that can be performed by protein, gene, and/or tissue array analysis.

Immunohistochemistry is preferred. RT-PCR on whole extracts may also be advantageous, as well as FISH techniques in situ.

In the in vitro methods, the biological sample may be any fluid, e.g. blood, or tissue sample of the patient. Preferably the biological sample is a tumor sample, especially a sample of the tumor tissue, especially when the tumor is a solid tumor. Indeed the in vitro methods are preferably performed on tumor biopsy or complete or partial cancer surgical resection. In another embodiment, expression of Rad18 may also be detected in a blood sample of a patient affected with a tumor. Indeed, cancer cells (including CSC) are well known to circulate in blood (Mavroudis 2010; Alix-Panabières et al., 2013).

In another embodiment, imaging techniques (e.g. RMI, nuclear medicine imaging notably PET . . . ) may be used, especially to detect Rad18 expression in brain tumors, using an imaging agent that is specific of Rad18.

The below Experimental section illustrates the invention without limiting its scope:

Example 1: Association of Rad18 with the Stem Cell State of Cancerous Cells

Materials and Methods

Xenopus Egg Extracts Preparation and Use

Interphasic and cycling Xenopus egg extracts were prepared and used as described (Murray et al, 1991; Recolin et al, 2012). UV-irradiation of sperm chromatin and isolation of chromatin fractions was as described (Recolin et al, 2012). For experiments performed at low N/E ratio, sperm nuclei (1000 nuclei/µl) were diluted 10-fold in XB buffer (100 mM KCl; 10 mM Hepes-KOH, pH 7.7; 2 mM MgCl2; 0.1 mM CaCl2; 50 mM sucrose, pH 7.7) supplemented with proteases inhibitors (leupeptin, aprotinin and pepstatin, 5 µg/ml each) on ice, and added to the same volume of cytoplasm as for the high N/E ratio condition.

Immunodepletion and Immunoprecipitation Procedures

Rad18 was removed from egg extracts by two rounds of depletion with affinity-purified Rad18 antibodies coupled to DynaBeads (Invitrogene). This procedure allows minimal dilution of the extracts during the depletion procedure avoiding spontaneous checkpoint activation likely due to dilution of the Rad6-Rad18 complex. Egg supernatants were thawed and supplemented with cycloheximide on ice and beads were added to the extract in a 50% ratio (V:V). For immunoprecipitations, extracts were diluted ten-fold in XB buffer supplemented with protease inhibitors and incubated with Rad18 antibody for 1 hour at 4° C. Immunocomplexes were collected with Protein A sepharose, washed in XB buffer and neutralized in Laemmli buffer.

Cell Culture

NIH3T3, HEK 293T, HCT8, HCT116 and U87 cells were maintained in Dulbecco's modified eagle's medium (DMEM) supplemented with 10% fetal bovine serum, 2 mM glutamine and antibiotics in a humidified atmosphere of 5% CO2 at 37° C. For transient expression of Rad18 or empty vector (pcDNA3), HEK 293T cells were transfected using calcium phosphate. Twenty-four hours after transfection cells were mock- or UV-irradiated using a microprocessor-controlled crosslinker (BIO-LINK®). Cells were collected at indicated time points after treatment and rinsed once in PBS. Whole cell extracts were clarified by centrifugation at 12000 g for 10 min at 4° C. Protein concentration of the clarified lysates was estimated using BCA method (Pierce). Equal amount of protein was used for western blot analysis.

Immunofluorescence Microscopy

Cells were grown on coverslips prior to co-transfection. Four hours after UV-C irradiation, cells were fixed with 3.2% paraformaldehyde for 15 min at room temperature and washed three times with PBS. After washing twice with PBS+3% BSA, cells were mounted with ProlongGold DAPI (Invitrogen). eGFP-Polη foci were analyzed with Leica DM6000 epifluorescence microscope (RIO imaging facility). Images were acquired using a Coolsnap HQ CCD camera (Photometrics) and metamorph software (Molecular Devices).

Foci Formation Assay

Cells were co-transfected with eGFP-Polη and Rad18 variants and incubated for 24 hours before UV-C irradiation. Four hours after irradiation, cells were fixed, washed three times with PBS, and mounted with Prolong Gold DAPI (Invitrogen). The percentage of eGFP-Polη-expressing cells displaying eGFP-Polη foci was determined by scoring at least 200 nuclei for each condition. Nuclei containing under 30 foci were scored as negatives. Means and standard deviation (error bars) of three independent experiments are shown.

For scoring RPA foci, cells were fixed with 4% paraformaldehyde and extracted with 0.5% Triton X-100 for 5 minutes at 4° C., then blocked for 30 minutes at room temperature with PBS/3% BSA/15% FBS, followed by detection of RPA by indirect immunofluorescence with specific antibodies (ab2175).

siRNA

U87 cells were co-transfected either with siRNA Rad18 (GAG GAU UCU UCU AGC UGU A; SEQ ID NO:3) or siRNA Luciferase (Luc) as a control and an empty vector (pcDNA3) or Rad18 expressing vector using JETPrime reagent (Polyplus). Twenty-four hours after transfection, cells were trypsinized and seeded in 12 wells plates at a density of 10 000 cells/well. Twenty-four hours later cells were treated with increasing concentration of cisplatin (Sigma).

Cell Viability Experiments

Cells were plated at 1×104 per well in twelve-well plates and UV-irradiated or exposed to the indicated amount of cisplatin (CisPt, Sigma). 48 hours after irradiation, cell viability was determined using the CellTiter-Glo® Luminescent Cell Viability assay (Promega).

RNA Extraction, Reverse Transcription and Quantitative Real-Time PCR

Total RNA was isolated with TRIzol reagent (Invitrogen). Reverse transcription was carried out using random hexa-nucleotides (Sigma) and Superscript II First-Strand cDNA synthesis kit (Invitrogen). Quantitative PCR reactions were performed using Lightcycler SYBR Green I Master mix (Roche) on Lightcycler apparatus (Roche). All primers used were intron spanning and to ensure specificity melt-curve analysis were carried out at the end of all PCR reactions (primer sequences available upon request). The relative amount of target cDNA was obtained by normalisation using geometric averaging of an internal control gene (HPRT).

Patients and Tumor Samples.

Tumor sample were obtained from patients diagnosed for type IV grade glioma (i.e. glioblastoma) and undergoing surgery at the neurosurgery department of the Rangueil Hospital (Toulouse, France). All subjects provided their informed written consent before their surgery and the protocol followed the declaration of Helsinki guidelines and was approved by local ethics committee.

Results

Inhibition of Replication Fork Uncoupling at Low N/E Ratio in Xenopus Egg Extracts Egg extracts supplemented with less than 400 nuclei per microliter (low N/E ratio) do not activate a checkpoint signal in the presence of unreplicated DNA. Checkpoint activation is observed with 1000-3000 sperm nuclei per microliter, which correspond roughly to the concentration of nuclei found in embryos at stage 7 when a cell cycle delay in response to unreplicated DNA is first observed. In line with previous observations in vivo (Kappas, et al, 2000; Conn et al, 2004), we observed no Chk1 phosphorylation when UV-irradiated sperm nuclei are present at low N/E ratio in egg extracts naturally synchronized in very early S-phase (FIG. 1A, upper panel, lane 2), nor delayed onset of mitosis, as monitored by phosphorylation of MCM4, a CDK1 substrate (Hendrickson, et al 1996). In addition, UV-irradiated sperm chromatin did not delay DNA synthesis when present at low N/E ratio in egg extracts, while a slow down is observed at high N/E ratio, as a result of ATR-dependent phosphorylation of the Chk1 protein kinase (Byun, et al, 20).

Altogether these results confirm checkpoint silencing and show that the in vitro system closely recapitulates the developmental activation of the checkpoint observed in vivo. UV photoproducts halt the progression of replicative DNA polymerases but not that of the helicase at replication forks, thus resulting in production of long stretches of single-stranded (ss)DNA, (replication fork uncoupling, Byun, et al, 2005) considered as the primary substrate that initiates checkpoint signaling. Accumulation of the ssDNA binding protein RPA serves as a convenient readout for replication fork uncoupling and ssDNA formation. FIG. 1A (lower panel) shows that while RPA greatly accumulates in S-phase onto UV-irradiated chromatin supplemented at high N/E ratio, as expected (lanes 3-4), very little RPA accumulation occurs at low N/E ratio (lanes 1-2), suggesting inefficient replication fork uncoupling. Consistent with this possibility, accumulation of the ATR-interacting protein ATRIP, recruited by RPA and required for checkpoint signaling is also strongly abolished, while its recruitment is normally observed upon UV irradiation at high N/E ratio. ATR was bound to chromatin at both low and high N/E ratios and modestly accumulated upon UV irradiation at low N/E ratio, similar to ATRIP. Because efficient replication fork uncoupling is observed at low N/E ratio by blocking DNA synthesis with aphidicolin, an inhibitor of replicative DNA polymerases, it suggests that the uncoupling defect is specific to UV damage.

Translesion (TLS) DNA polymerases can replicate damaged DNA, and TLS Polη replicates past UV lesions (Sale et al, 2012). We observed that Polη is chromatin-associated even in the absence of UV-damage at low N/E ratio, and its recruitment did not change upon UV-irradiation (FIG. 1A, lower panel, lanes 1-2). In contrast, Polη was not chromatin-bound at high N/E ratio without UV-damage (lane 3) and was recruited upon UV-irradiation (lane 4). We have also verified that other replicative polymerases are present on chromatin at low N/E ratio. Quantification of Polη bound to chromatin at low N/E ratio compared to recombinant Polη indicates that it is present at a similar level than Polη. Strikingly, constitutive PCNAmUb was observed irrespective of DNA damage at low N/E ratio (FIG. 1A, lanes 1-2) while at high N/E ratio PCNAmUb was observed mainly upon UV irradiation (lane 4, lower panel), as previously reported (Chang et al, 2006). Finally, we observed inhibition of constitutive Polη recruitment at low N/E ratio (in the absence of external damage) by Geminin, an inhibitor of pre-replicative complexes. Since recruitment of Polη also depends upon PCNA, it suggests that its constitutive chromatin binding at low N/E ratio requires functional replication forks.

The Rad6-Rad18 Ubiquitin Ligase and not Polη is Titrated from Egg Extract at High N/E Ratio Maternally-supplied inhibitor(s), present in limited amount in the egg cytoplasm and progressively titrated into nuclei produced during the embryonic cleavages, may be responsible for checkpoint silencing (FIG. 1B). Hence, abundance of the(se) factor(s) in egg extracts is expected to be reduced at high N/E ratio. Data shown in FIG. 1A, and previous data in *C. elegans* (Holway et al, 2006; Ohkumo et al, 2006) implicate components of the TLS pathway. FIG. 10 shows that the relative amount of PCNA, Polη, USP1, RPA, Chk1 and ATR present in the extract (unbound) after incubation with sperm nuclei is the same irrespective of N/E ratio, suggesting that they are in excess over the DNA. To investigate the abundance of Rad6 and Rad18 we cloned the corresponding genes and raised antibodies against a recombinant form of each protein. Interestingly, we observed that the abundance of Rad6 and Rad18 left in the extract after incubation with sperm nuclei at high N/E ratio dramatically decreased (FIG. 10) being also less abundant on chromatin (FIG. 1D), concomitant to reduced PCNAmUb and absence of Polη chromatin binding. This reduction is unlikely due to degradation since the level of Rad18 in the unfractionated sample (unbound+chromatin) was similar at high versus low N/E ratio, suggesting that Rad6 and Rad18 were titrated out from the extract at high N/E ratio. Quantification of Rad18 stored in *Xenopus* eggs shows that its concentration is relatively low (~0.5 ng/μl of egg extract), which is between 100-200 times less abundant than PCNA, suggesting that Rad6-Rad18 is stored in the *Xenopus* egg in limited amount compared to PCNA, Polη, kinase (ASK) and Rad18 is essential for chromatin recruitment of Rad18 after DNA damage (Yamada et al, 2013). In early *Xenopus* development the Dbf4-related Drf1 protein is implicated in DNA synthesis (Takahashi et al, 2005; Collart et al, 2013). We observed a Rad18-Drf1 complex in egg extracts at low N/E ratio in the absence of external damage. Strikingly, this complex was virtually undetectable at high N/E ratio (FIG. 1E), although the amount of Drf1 present in the unbound fraction at low versus high N/E ratio did not significantly change. These results suggest that complex formation with Drf1 may enhance Rad18 chromatin recruitment at low N/E ratio.

To investigate whether constitutive PCNAmUb may be responsible for constitutive Polη chromatin association and checkpoint repression at low N/E ratio, we removed Rad18 from egg extracts with Rad18-specific antibodies. Depletion of Rad18 also partially removed Rad6 as expected (FIG. 2A), but not Polη, PCNA nor RPA. Rad18 depletion drastically reduced PCNAmUb induced by UV-irradiated nuclei at low N/E ratio, as well as Polη chromatin binding, and importantly induced UV-damage-dependent Chk1 phosphorylation (FIG. 2B, lane 3). Checkpoint repression could be restored by reconstitution of Rad18-depleted extracts (FIG. S2F) with recombinant 6His-Rad6-Rad18 (FIG. 2C), thus excluding the implication of co-depleted proteins (FIG. 2D, lane 5). This complex, and not recombinant Rad6, also rescued defective PCNAmUb in Rad18-depleted egg extracts, demonstrating that it is functional. Because either Rad6 or Rad18 mutant cells are Nucleotide Excision Repair (NER)-proficient, it makes unlikely that Chk1 phosphorylation observed at low N/E upon Rad18 depletion results from accumulation of unrepaired DNA. Further, removal of Rad18 did not increase normal Chk1 phosphorylation observed at high N/E ratio compared to the control, indicating that this phenotype is specific to low N/E ratio. Furthermore, addition of recombinant PCNA mutated in the residue monoubiquitylated by Rad6-Rad18 (K164R), and not wild-type PCNA (WT), induced UV-dependent Chk1 phosphorylation in egg extracts at low N/E ratio. Of note, we did not observe chromatin binding of the very recently discovered Primpol at low N/E ratio, ruling out active bypass of UV lesions by this enzyme. Finally, increasing Rad6-Rad18 abundance at high N/E ratio by addition of recombinant 6His-Rad6-Rad18, in which UV-dependent checkpoint activation occurs (FIG. 2E, lane 2), induced repression of Chk1 phosphorylation (lane 3) as well as significant repression of UV-dependent RPA accumulation (compare lanes 2 and 3, and panel F) suggesting inhibition of replication fork uncoupling. These data altogether show that Rad18-Rad6 is responsible for constitutive Polη chromatin binding at low N/E ratio and that its removal is sufficient to give the competence to activate the checkpoint upon UV-irradiation.

Reactivation of an Embryonic-Like Checkpoint State in Mammalian Cells by Ectopic Expression of Rad18

Next we analyzed the consequences of increasing Rad18 abundance in somatic mammalian cells. Rad18 overexpression did not induce significant cell cycle changes, and consistent with two previous reports (Davies et al, 2008; Bi et al, 2006) we observed constitutive PCNAmUb (FIG. 3A). Importantly overexpression of either Rad6, or Rad18 and Rad6 was not sufficient to induce significant PCNAmUb. Interestingly, and similar to what observed in *Xenopus*, eGFP-Polη accumulated into nuclear foci even in the absence of DNA damage only upon overexpression of Rad18 (FIG. 3B-C). Most importantly, we observed significant repression of Chk1 phosphorylation induced by UV irradiation in asynchronous cells expressing Rad18 (FIG. 3D), suggesting that high Rad18 expression in mammalian cells is sufficient to suppress UV-dependent checkpoint activation, in line with a previous observation in yeast (Daigaku et al, 2010). Expression of a Rad18 mutant lacking the residues phosphorylated by the Cdc7 kinase (Rad18Δ401-445) and required for Polη binding (Durando et al, 2013) did not induce spontaneous eGFP-Polη nuclear foci, consistent with a previous report (Day et al, 2010). Importantly this mutant did not either suppress Chk1 phosphorylation (panel D), suggesting that repression of the checkpoint depends upon Rad18 interaction with Polη and phosphorylation by Cdc7. We next determined whether cells expressing Rad18 display increased resistance to DNA damage as a result of impaired checkpoint activation. To this end we generated stable cell lines expressing low levels of Rad18 wild-type or a mutant in the ring-finger domain (C28F). FIG. 5A shows that expression of Rad18 wild-type and not the C28F mutant significantly increased the viability of cells upon UV damage or upon exposure to the chemotherapy-relevant drug cisplatin (FIG. 5B). Taken together these results link Rad18 expression to resistance to DNA damaging agents.

Rad18 is Overexpressed in Cancer Cells Resistant to DNA Damage

Resistance to DNA damaging agents is a feature of cancer cells implicated in cancer recurrence. To explore the link between high Rad18 expression, resistance to DNA damaging agents and cancer, we analyzed Rad18 expression in different cancer cell lines and observed high Rad18 abundance in a colon cancer-derived cell line resistant to oxaliplatin (HCT116) compared to the oxaliplatin-sensitive HCT8 cancer cell line (FIG. 5C), as well as in the highly DNA damage-resistant brain cancer glioblastoma (FIG. 4A). Importantly, we observed high Rad18 expression specifically in glioblastoma cancer stem cells isolated from tumor biopsies (CD133+, also known as tumor initiating cells), and not in their differentiated counterparts (CD133−) that express Rad18 to similar levels than Hela cells (FIG. 4B). In contrast, expression of Rad6 and other TLS-, checkpoint- and proliferation-relevant proteins was not increased in glioblastoma (FIG. 4B). Further, downregulation of Rad18 expression in the U87 glioblastoma cell line induced a strong sensitivity to cisplatin (FIG. 4C). Importantly, not only this phenotype was completely rescued by re-expression of Rad18, but cells also showed a dramatic increased viability, suggesting acquired resistance to cisplatin. Since glioblastoma are normally resistant to this drug, these observations make of Rad18 a novel target to sensitize glioblastoma to cisplatin treatment. Altogether these findings suggest that increased Rad18 expression has a positive effect on proliferation upon DNA damage by shunting checkpoint activation thus conferring resistance to DNA damage (FIG. 4D), and show high Rad18 expression specifically in cancer stem cells that are strongly implicated in the resistance to the therapy.

Example 2: Rad18 Downregulation Affects the Proliferation of Glioblastoma Cancer Stem Cells in the Absence of External Damage Materials and Methods Glioblastoma cancer stem cells (Gliospheres, Gb4 and Gb7 cell lines) were isolated from patients as described in Clarion et al, 2014.

Cells were maintained in DMEM-F12 (Lonza, Levallois-Perret, France) supplemented with B27 and N2 (Invitrogen, LifeTechnologies, Saint Aubin, France), 25 ng/ml of FGF-2 and EGF (Peprotech, Neuilly sur Seine, France) at 37° C. in 5% CO2 humidified incubators.

Results

Gb4 glioblastoma cancer stem cells extracts, treated with control siRNA or a Rad18-specific siRNA (SEQ ID NO:3) were analysed 72 hours post-treatment. Extracts were probed with anti-Rad18 or anti-PCNA antibodies, the Western Blot is shown on FIG. 6 (A).

FIG. 6 (B) shows phase contrast microscopy images of the gliospheres. Downregulation of Rad18 expression was shown to affect the proliferation of gliospheres (see also FIG. 6 C, for quantification).

Example 3: The USP7 Inhibitor P2207 Sensitizes Glioblastoma to Cisplatin Treatment Materials and Methods
Cell Viability Experiments Cells were plated at $1.0 \times 10^4$ cells/well in 12-well plates and exposed to the indicated amount of P2207 inhibitor (Sigma) or DMSO as control. 48 h post-treatment, cell viability was determined using the CellTiter-Glo luminescent cell viability assay (Promega).

Results

Cell viability of U87-MG glioblastoma cells treated with USP7 inhibitor P2207 was assessed. As shown on FIG. 7, the USP7 inhibitor P2207 sensitizes glioblastoma to cisplatin treatment.

REFERENCES

Alix-Panabières C., Pantel K. Clin Chem. 2013, 59(1):110-8;
Barrangou (2013) Wiley Interdiscip Rev RNA. 4(3):267-278;
Bartkova et al, 2005, Nature, 434(7035):864-70;
Bi et al., Mol Cell Biol 26, 3527 (2006);
Byun, et al, Genes Dev 19, 1040 (2005);
Ciccia and Elledge, 2010, Mol Cell. 2010 Oct. 22; 40(2): 179-20
Chang, et al, J Biol Chem 281, 32081 (2006);
Christian, et al. (2010) Genetics 186:757-761;
Clarion et al, 2014, J Med Chem. 23; 57(20):8293-306;
Collart, et al, Science 341, 893 (2013);
Conn et al, Dev Cell 7, 275 (2004);
Daigaku, A. Nature 465, 951 (2010);
Davies, et al, Mol Cell 29, 625 (2008);
Day et al, The Journal of cell biology 191, 953 (2010);
Durando, Nucleic acids research 41, 3079 (2013);
Gaj et al, 2013, Trends in biotechnology, 31(7):397-405;
Gorgoulis et al, 2005, Nature, 434(7035):907-13;

Hendrickson, et al, Proc. Natl. Acad. Sci. USA 93, 12223 (1996);
Holway, et al, J Cell Biol 172, 999 (2006);
Jinek et al. (2013) Science 337 (6096): 816-821;
Huang et al., Nat Cell Biol 11, 592 (2009);
Hwang et al., Biomaterials, 32: 4968-4975, 2011;
Kannouche et al., Mol Cell 2004 21; 14(4):491-500;
Kappas, et al, Mol Biol Cell 11, 3101 (2000);
Larson et al. (2013) Nature Protocols 8 (11): 2180-2196;
Lee et al, 2006 Cancer Cell. 9(5):391-403;
Li, et al. (2010) Nucleic Acids Res. 39(1):359-372;
Mavroudis D. Ann Oncol. 2010 21 suppl 7: vii95-100;
Murray, Methods in Cell Biology 36, 581 (1991);
Ohkumo et al, Cell Struct Funct 31, 29 (2006);
Recolin et al, Nucleic Acids Res 40, 3431 (2012);
Richter et al. (2013) Int J Mol Sci. 14(7): 14518-31;
Rohn et al., J. Drug Target, 20: 381-388, 2012;
Sale, et al. Nat Rev Mol Cell Biol 13, 141 (2012);
Singh et al, 2003, Cancer Res. 63(18):5821-8;
Stupp et al, 2009, Lancet Oncol. 10(5):459-66;
Takahashi, et al, Genes & development 19, 2295 (2005);
Watanabe et al., 2004 EMBO J 23, 3886-3896;
Watanabe et al., Nucleic Acids Res 37, 2176 (2009).
Yamada et al., Genes & development 27, 2459 (2013).

The invention claimed is:

1. A method for treating a tumor that is resistant to a treatment with a DNA damaging antineoplastic agent, in a patient, said method comprising administering to a patient in need thereof a therapeutically effective amount of an inhibitor of Rad18 expression.

2. The method according to claim 1, wherein the tumor is a tumor that comprises cancer stem cells, whereby the inhibitor kills said cancer stem cells, reduces self-renewal of said cells and/or decreases the growth of said cells.

3. The method according to claim 1, for reducing the risk of cancer relapse in the patient.

4. The method according to claim 1, for sensitizing a patient affected with a tumor that is resistant to a treatment with a DNA damaging antineoplastic agent, wherein the tumor becomes sensitive to said antineoplastic agent.

5. The method according to claim 1, wherein the antineoplastic agent is selected from the group consisting of a platinum compound, an alkylating agent, and a topoisomerase inhibitor.

6. The method according to claim 1, wherein the inhibitor is administered within one day to one week before the patient is administered with said antineoplastic agent.

7. The method according to claim 1, wherein the inhibitor of Rad18 expression is a nucleic acid that inhibits the expression of Rad18.

8. The method according to claim 1, wherein the inhibitor of Rad18 expression is selected from the group consisting of a zinc-finger nuclease (ZFN), a transcription-activator like effector nuclease (TALEN), and a RNA-guided DNA endonuclease.

9. The method according to claim 1, wherein the tumor is of embryonic origin or generated by dedifferentiation of somatic cells.

10. The method according to claim 1, wherein the tumor is selected from the group consisting of a glioblastoma, colorectal carcinoma, lung cancer, breast cancer, ovarian cancer and leukemia.

11. The method of claim 5, wherein the platinum compound is selected from the group consisting of cisplatin, carboplatin, oxaliplatin, arboplatin, nedaplatin, and satraplatin.

12. The method of claim 5, wherein the alkylating agent is methylmethane sulfonate.

13. The method of claim 5, wherein the topoisomerase inhibitor is camptothecine.

14. The method of claim 7, wherein the nucleic acid that inhibits the expression of Rad18 is selected from the group consisting of small interfering RNA (siRNA), small hairpin RNA (shRNA), micro RNA (miRNA), an aptamer, a ribozyme, and an antisense oligonucleotide.

* * * * *